(12) United States Patent
Rady

(10) Patent No.: US 11,022,986 B2
(45) Date of Patent: Jun. 1, 2021

(54) PIPELINE INTERCHANGE

(71) Applicant: PHILLIPS 66 COMPANY, Houston, TX (US)

(72) Inventor: Paul Rady, Katy, TX (US)

(73) Assignee: Phillips 66 Company, Houston, TX (US)

( * ) Notice: Subject to any disclaimer, the term of this patent is extended or adjusted under 35 U.S.C. 154(b) by 48 days.

(21) Appl. No.: 16/391,817

(22) Filed: Apr. 23, 2019

(65) Prior Publication Data

US 2019/0339724 A1    Nov. 7, 2019

Related U.S. Application Data

(60) Provisional application No. 62/667,694, filed on May 7, 2018.

(51) Int. Cl.
| | | |
|---|---|---|
| *G05D 7/06* | (2006.01) | |
| *G01N 33/28* | (2006.01) | |
| *F17D 3/01* | (2006.01) | |

(52) U.S. Cl.
CPC .............. *G05D 7/0652* (2013.01); *F17D 3/01* (2013.01); *G01N 33/28* (2013.01); *Y10T 137/2509* (2015.04); *Y10T 137/87877* (2015.04)

(58) Field of Classification Search
CPC .................. G05D 7/0652; G01N 33/28; Y10T 137/87877; Y10T 137/2506; Y10T 137/2509; F17D 3/01
USPC ............................................. 137/92, 93, 883
See application file for complete search history.

(56) References Cited

U.S. PATENT DOCUMENTS

| | | | | | |
|---|---|---|---|---|---|
| 3,464,447 | A | * | 9/1969 | Jones ...................... | F16K 11/22 137/883 |
| 5,159,957 | A | * | 11/1992 | Hehl ....................... | B29C 45/72 137/883 |
| 6,019,003 | A | * | 2/2000 | Wieder .................... | G01F 1/10 73/861.77 |
| 6,076,049 | A | * | 6/2000 | Lievois .............. | G01N 33/2823 702/100 |
| 6,321,782 | B1 | * | 11/2001 | Hollister ............... | F17C 13/025 137/557 |
| 6,679,302 | B1 | | 1/2004 | Mattingly et al. | |
| 7,032,629 | B1 | | 4/2006 | Mattingly et al. | |
| 7,306,115 | B2 | * | 12/2007 | Beachy ................... | G01F 1/103 137/487.5 |

(Continued)

*Primary Examiner* — William M McCalister
(74) *Attorney, Agent, or Firm* — Phillips 66 Company

(57) ABSTRACT

The present embodiment describes a pipeline interchange, wherein the pipeline interchange has a refined petroleum product flowing through an upstream pipeline. The pipeline interchange can also have an automated slipstream analyzer connected to the upstream pipeline comprising an inlet, a return and an analyzer. In this embodiment, the automated slipstream analyzer is used to collect a sample, analyze the sample, generate data from the sample and return the sample of the refined petroleum product flowing through the upstream pipeline. The pipeline interchange can also have an automatic splitter, downstream of the automated slipstream analyzer, capable of receiving and interpreting the data from the automated slipstream analyzer and directing the refined petroleum product into at least three different downstream pipelines, wherein at least one of the downstream pipelines is an intermix pipeline.

17 Claims, 2 Drawing Sheets

(56) References Cited

U.S. PATENT DOCUMENTS

| | | | | |
|---|---|---|---|---|
| 7,628,080 B1* | 12/2009 | Feller | ............ | G01F 1/588 |
| | | | | 73/861.12 |
| 7,631,671 B2 | 12/2009 | Mattingly et al. | | |
| 7,886,616 B1* | 2/2011 | Hayman | ............ | G01F 1/115 |
| | | | | 73/861.78 |
| 9,324,228 B2* | 4/2016 | Trout | ............ | G08B 19/02 |
| 9,494,948 B2 | 11/2016 | Mattingly et al. | | |
| 2006/0102133 A1* | 5/2006 | Callan | ............ | F01M 1/18 |
| | | | | 123/196 R |
| 2008/0000529 A1* | 1/2008 | Lawrence Edwards | ............ | |
| | | | | F16K 17/02 |
| | | | | 137/455 |
| 2008/0156077 A1* | 7/2008 | Flanders | ............ | E21B 33/03 |
| | | | | 73/49.6 |
| 2013/0291974 A1* | 11/2013 | Bourgeois | ............ | F17D 5/005 |
| | | | | 137/625.3 |
| 2013/0340536 A1* | 12/2013 | Shyy | ............ | G01F 1/28 |
| | | | | 73/861.71 |
| 2014/0144541 A1* | 5/2014 | Moreira De Carvalho | ............ | |
| | | | | C22C 38/04 |
| | | | | 138/177 |
| 2014/0152977 A1* | 6/2014 | Ranftl | ............ | G01N 21/61 |
| | | | | 356/51 |
| 2014/0352399 A1* | 12/2014 | Vaissiere | ............ | G01F 25/0007 |
| | | | | 73/1.34 |
| 2015/0153746 A1* | 6/2015 | Lee | ............ | B01D 3/008 |
| | | | | 137/883 |
| 2015/0192442 A1* | 7/2015 | Olin | ............ | G01F 1/69 |
| | | | | 73/204.26 |
| 2015/0192443 A1* | 7/2015 | Olin | ............ | G01F 1/692 |
| | | | | 73/204.26 |
| 2015/0276448 A1* | 10/2015 | Nyhart, Jr. | ............ | G01F 1/7086 |
| | | | | 73/861.05 |
| 2017/0166825 A1* | 6/2017 | Mattingly | ............ | C10L 1/06 |

\* cited by examiner

PIPELINE INTERCHANGE

CROSS-REFERENCE TO RELATED APPLICATIONS

This application is a non-provisional application which claims the benefit of and priority to U.S. Provisional Application Ser. No. 62/667,694 filed May 7, 2018, titled "Pipeline Interchange," which is hereby incorporated by reference in its entirety.

STATEMENT REGARDING FEDERALLY SPONSORED RESEARCH OR DEVELOPMENT

None.

FIELD OF THE INVENTION

This invention relates to a pipeline interchange

BACKGROUND OF THE INVENTION

Pipelines transport different types of refined petroleum product in the same pipeline. To do so, a pipeline operator sends different products in "batches". For example, an operator might send gasoline for several hours, and then switch to jet fuels, before switching to diesel fuel. The process of tracking the customer's batch or product through the pipeline is done through analyzing the different products within a pipeline.

Throughout the process, the product is measured at the receipt point in the pipeline and again upon delivery to document the amount of product moved from point A to point B. Many pipeline systems require pipeline owners to meet defined common product specifications for each product shipped. This requires pipeline owners to regularly analyzing many different properties of refined products in a refinery or a terminal. In these scenarios, a sample of refined product is analyzed either before entering the pipeline or during to give an analytical result. Once the area in which the sample is taken from reaches a splitter, the operation of the splitter is adjusted based on the properties of the refined product.

Current analytical techniques, in a pipeline, require that the sample of refined product are taken with a hydrometer and adhere to ASTM guidelines such as ASTM 287. To adhere to these guideline pipeline operators must take the sample by either stopping the flow of a pipeline or taking a sample from a flowing pipeline. Stopping a pipeline is expensive and not ideal. Taking a sample from a flowing pipeline can mean large quantities of the refined product can flow through the pipeline prior to the analytical results being generated.

A pipeline interchange is generally known in the industry as a location where products that flow through a pipeline are separated. In refined petroleum industry, this pipeline interchange generally consists of substantially horizontal pipes that operate within either a pipeline terminal, a refinery, a marine dock, or a rail terminal. Typically, one pipeline will be tasked with transporting various refined petroleum products and a method of separating the refined petroleum products within the pipeline to different pipelines or storage compartments is required.

There exists a need for a configuration that would allow a pipeline operator to obtain near instantaneous analytical results from a sample of refined product and relay that information to a splitter.

BRIEF SUMMARY OF THE DISCLOSURE

The present embodiment describes a pipeline interchange, wherein the pipeline interchange has a refined petroleum product flowing through an upstream pipeline. The pipeline interchange can also have an automated slipstream analyzer connected to the upstream pipeline comprising an inlet, a return and an analyzer. In this embodiment, the automated slipstream analyzer is used to collect a sample, analyze the sample, generate data from the sample and return the sample of the refined petroleum product back to the pipeline. The pipeline interchange can also have an automatic splitter, downstream of the automated slipstream analyzer, capable of receiving and interpreting the data from the automated slipstream analyzer and directing the refined petroleum product into at least three different downstream pipelines, wherein at least one of the downstream pipelines is an intermix pipeline.

In another embodiment, the pipeline interchange can also comprise a refined petroleum product flowing through an upstream pipeline. In this embodiment, the refined petroleum product comprises: gasoline, diesel and the intermix of gasoline and diesel. Connected to the upstream pipeline an automated slipstream analyzer is operated simultaneously comprising an inlet, a return and an analyzer. The automated slipstream analyzer is used to continuously collect samples, continuously analyze samples, continuously generate data from the samples and continuously return the sample of the refined petroleum product flowing through the upstream pipeline. In this embodiment, the automated slipstream analyzer can be an infrared analyzer or a near infrared analyzer. Downstream of the automated slipstream analyzer an automatic splitter capable of responding to the data from the automated slipstream analyzer and directing the refined petroleum product into a gasoline pipeline, a diesel or other distillate pipeline, and an intermix pipeline.

In yet another embodiment, a method is taught of flowing a refined petroleum product through an upstream pipeline. The method then continuously analyzes a sample of the refined petroleum product to generate data. With this data, the flow is adjusted of the refined petroleum product towards one of at least three different downstream pipelines depending upon the data, wherein at least one of the downstream pipelines is an intermix pipeline.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
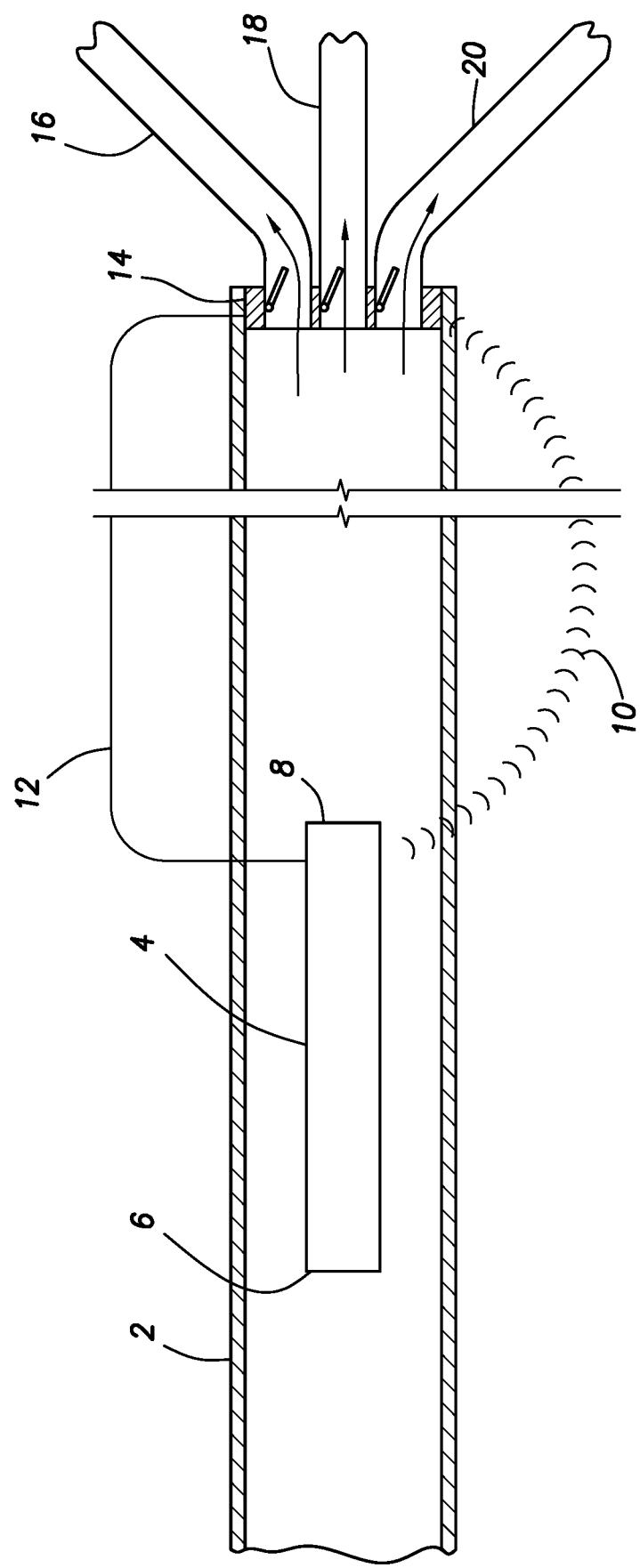
FIG. 1 depicts one embodiment of the pipeline interchange.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

The present embodiment describes a pipeline interchange, wherein the pipeline interchange has a refined petroleum product flowing through an upstream pipeline. The pipeline interchange can also have an automated slipstream analyzer connected to the upstream pipeline comprising an inlet, a return and an analyzer. In this embodiment, the automated slipstream analyzer is used to collect a sample, analyze the sample, generate data from the sample and return the sample of the refined petroleum product flowing through the upstream pipeline. The pipeline interchange can also have an automatic splitter, downstream of the automated slipstream analyzer, capable of receiving and interpreting the data from the automated slipstream analyzer and directing of directing the refined petroleum product into at least three different downstream pipelines, wherein at least one of the downstream pipelines is an intermix pipeline.

In this embodiment, an upstream pipeline is generally defined as the pipeline upstream of the pipeline interchange and a downstream pipeline is generally defined as the pipeline downstream of the pipeline interchange.

In one embodiment, the pipeline interchange is an integral part of a pipeline terminal or a refinery. A pipeline interchange is generally thought of as a place where different pipelines can either intersect or diverge. The size of the upstream pipeline and downstream pipelines can vary based upon the products they are transporting. In one embodiment, the upstream pipeline and the downstream pipeline can range from about 4 inches in diameter to about 48 inches in diameter. These pipelines can either flow downstream of the pipeline interchange into other pipelines, into storage containers or storage tanks, into marine vessels, or into rail cars. These medians can also include an intermix. In one embodiment, at least three different downstream pipelines can be connected to pipeline storage tanks or intermix storage tanks.

In other embodiments, there can be two different downstream pipelines, three different downstream pipelines, four different downstream pipelines, five different downstream pipelines, six different downstream pipelines or more. The number of different downstream pipelines will depend upon the different types of refined petroleum products flowing through the upstream pipeline. In other embodiments, the one of the downstream pipelines can be dedicated for contaminates. In yet another embodiment, the downstream pipelines can be interchangeable for their uses.

The refined product that flows through the pipelines can be any liquid or gaseous product that can be derived from crude oils through processes such as catalytic cracking and fractional distillation. These products can have physical and chemical characteristics that differ according to the type of crude oil and subsequent refining processes. Different types of refined petroleum products can include gasoline, diesel fuels, jet fuels, naphtha, marine gas oils, liquefied petroleum gasses, kerosene, lubricating oils and different types of fuel oils such as No. 2, No. 4, No. 5, and No. 6.

It is envisioned, in one embodiment, that the flow of the refined product would not be decreased when flowing through the pipeline interchange.

In one embodiment of the invention the analyzer is an optical analyzer. Unlike hydrometers that manually measure the density of the refined petroleum product it is envisioned that the pipeline interchange will utilize a continuous optical analyzer. In one embodiment, the pipeline interchange operates without a hydrometer. Types of optical analyzers that can be used include, infrared analyzers and near-infrared analyzers. The quantitative data generated by these analyzers can include data for premium gasoline, jet fuel, diesel fuel and unleaded gasoline.

In one embodiment, the optical analyzers can be used to analyze contaminants in the refined product. These contaminants can be compounds such as: benzene, toluene, ethylbenzene, xylenes, methyl tertiary butyl ethers, sulfur, vanadium, iron, zinc, or even lead scavengers. In other embodiments, the optical analyzer can be used to analyze properties of refined products such as: octane numbers, research octane numbers, motor octane numbers, antiknock index, boiling point, density, viscosity, molecular type compositions, elemental analysis, freezing point, carbon residue, pour point, cloud point, vapor pressure, reid vapor pressure, flammability range, wax and asphaltene contents, cetane number, aniline point, and carbonto-hydrogen ratios.

By utilizing optical analyzers, the automatic splitter will be able to receive rapid and reliable data regarding the composition of the refined petroleum product that is flowing through the pipeline. Additionally, the samples taken and returned to the pipeline by the optical analyzers allow the refined petroleum product to be reused instead of conventional hand measurement methods that can modify the refined petroleum product and therefore make it unsuitable of being returned to the pipeline or being used as a conventional fuel.

It is theorized that by using a continuous optical analyzer that the data generated can be received and interpreted by the automatic splitter faster than conventional methods. The automatic splitter can then be able to determine the precise moment the refined petroleum product changes from one type of petroleum product to an intermix and from the intermix to another type of petroleum product. Intermix is defined as a random mixture of on-specification fuels that due to their mixing no longer meet a specific fuel specification, such intermix fluids can be directed to an intermix pipeline, which can be connected to an intermix storage tank, which will be redistributed back to a refinery to generate petroleum products that meet product specification requirements.

In other embodiments, it is envisioned that automatic splitter can then be able to determine the precise moment the refined petroleum product changes from one type of petroleum product to one that contains contaminates. The automatic splitter then would direct the contaminated refined product to a pipeline that can be redistributed back to a refinery instead of to storage tanks for consumer use.

The automatic splitter can be from 1 meter to 500 meters downstream of the automated slipstream analyzer. In one embodiment, the automatic splitter can be up to 1 kilometer, 2 kilometers or even 5 kilometers downstream of the automated slipstream analyzer. The automatic splitter can be any splitter capable of directing the flow of the upstream pipeline into the different downstream pipelines. This can consist of a valve on each of the downstream pipelines or a central splitter used to direct the flow of fluid into one or more of the downstream pipelines.

In one embodiment, the automated slipstream analyzer is located inline of the upstream pipeline. As shown in FIG. 1, a side profile of an upstream pipeline 2 is shown with an automated slipstream analyzer 4 deposed within. The automated slipstream analyzer has an inlet 6 capable of collecting a sample and a return 8 capable of returning the sample of refined petroleum product flowing through the upstream pipeline. The automated slipstream analyzer can analyze the sample collected from the inlet and generate data from the sample. The data generated from the automated slipstream analyzer can be transferred wirelessly 10 or by a wired connection 12 to an automatic splitter 14 located downstream of the automated slipstream analyzer. As depicted in this embodiment, automatic splitter comprises a valve on each of the downstream pipelines, in other embodiments this could be different. In one embodiment as shown in FIG. 1, the automatic splitter is able to direct the refined petroleum product into at least three different downstream pipelines 16, 18 and 20.

As depicted in FIG. 1, the automated slipstream analyzer is placed in the center of the upstream pipeline. It is understood that in different embodiments the automated slipstream analyzer can be placed anywhere within the upstream pipeline capable of collecting a sample of the refined petroleum product.

Figure 2:
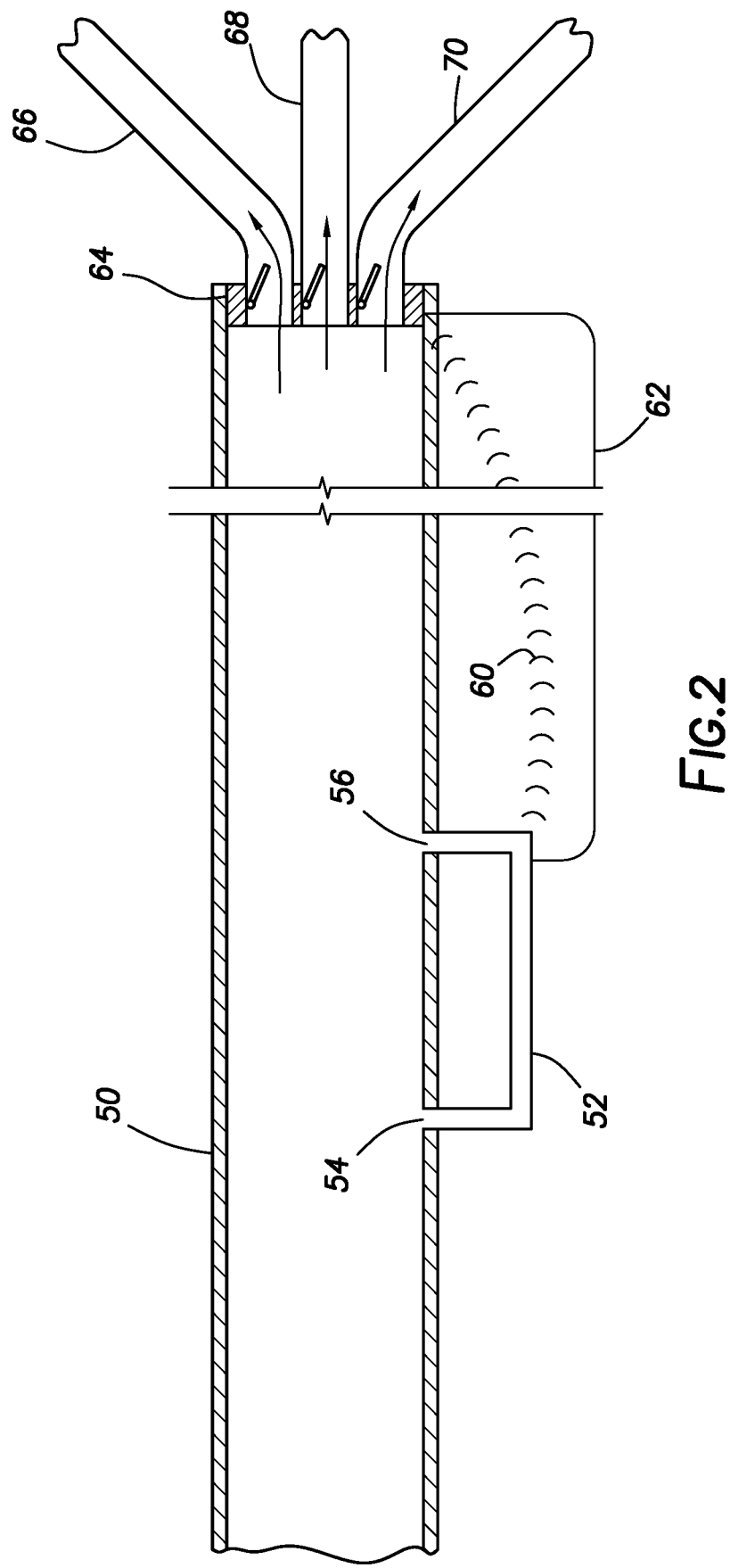
FIG. 2 depicts one embodiment of the pipeline interchange.

In another embodiment, the automated slipstream analyzer operates as a sample loop adjacent to the upstream pipeline. As shown in FIG. 2, upstream pipeline 50 has an automated slipstream analyzer 52 connected to the pipeline. The automated slipstream analyzer has an inlet 54 capable of collecting a sample and a return 58 capable of returning the sample of refined petroleum product flowing through the upstream pipeline. The inlet can be regulated to be a continuous flow or intermittent based on user needs. The automated slipstream analyzer can analyze the sample collected from the inlet and generate data from this sample. The data generated form the automated slipstream analyzer can be transferred wirelessly 60 or by a wired connection 62 to an automatic splitter 64 located downstream of the automated slipstream analyzer. As depicted in this embodiment, automatic splitter comprises a valve on each of the downstream pipelines, in other embodiments this could be different. In one embodiment as shown in FIG. 2, the automatic splitter is able to direct the refined petroleum product into at least three different downstream pipelines 66, 68 and 70.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A pipeline interchange comprising:
a refined petroleum product flowing through an upstream pipeline;
an automated slipstream analyzer connected to the upstream pipeline comprising an inlet, a return and an analyzer, wherein the automated slipstream analyzer is used to collect a sample, analyze the sample, generate data from the sample and return the sample of the refined petroleum product flowing through the upstream pipeline, and wherein the analyzer is capable of analyzing different chemical characteristics of the refined petroleum product;
an automatic splitter downstream of the automated slipstream analyzer, capable of receiving and interpreting the data from the automated slipstream analyzer and directing the refined petroleum product into at least three different downstream pipelines, wherein at least one of the downstream pipelines is an intermix pipeline and wherein each of the at least three downstream pipelines has a valve.

2. The pipeline interchange of claim 1, wherein the at least three different downstream pipelines are connected to pipeline storage tanks.

3. The pipeline interchange of claim 1, wherein the intermix pipeline is connected to an intermix storage tank.

4. The pipeline interchange of claim 1, wherein the refined petroleum products are selected from the group consisting of: gasolines, diesel fuels, jet fuels, naphtha, marine gas oils and liquefied petroleum gasses.

5. The pipeline interchange of claim 1, wherein the upstream pipeline can range from 4 inches in diameter to 48 inches in diameter.

6. The pipeline interchange of claim 1, wherein the refined petroleum product is liquid.

7. The pipeline interchange of claim 1, wherein the analyzer is an optical analyzer.

8. The pipeline interchange of claim 1, wherein the analyzer is an infrared analyzer or a near-infrared analyzer.

9. The pipeline interchange of claim 1, wherein the automated slipstream analyzer continuously analyzes the refined petroleum product.

10. The pipeline interchange of claim 1, wherein the automated slipstream analyzer does not modify the refined petroleum product.

11. The pipeline interchange of claim 1, wherein the automated slipstream analyzer operates in line with the upstream pipeline.

12. The pipeline interchange of claim 1, wherein the automated slipstream analyzer operates as a sample loop adjacent to the upstream pipeline.

13. The pipeline interchange of claim 1, wherein the splitter is from 1 meter to 500 meters downstream of the automated slipstream analyzer.

14. The pipeline interchange of claim 1, wherein the flow of refined product is not decreased when flowing through the pipeline interchange.

15. The pipeline interchange of claim 1, wherein the pipeline interchange operates within a refinery or a terminal.

16. The pipeline interchange of claim 1, wherein the pipeline interchange operates without a hydrometer.

17. A pipeline interchange comprising:
a refined petroleum product flowing through an upstream pipeline, wherein the refined petroleum product comprises: gasoline, diesel and an intermix of gasoline and diesel;
an automated slipstream analyzer operating simultaneously with the upstream pipeline comprising an inlet, a return and an analyzer, wherein the automated slipstream analyzer is used to continuously collect samples, continuously analyze samples, continuously generate data from the samples and continuously return the sample of the refined petroleum product flowing through the upstream pipeline and wherein the automated slipstream analyzer is an infrared analyzer or a near infrared analyzer, and wherein the analyzer is capable of analyzing different chemical characteristics of the refined petroleum product;

an automatic splitter, downstream of the automated slipstream analyzer, capable of receiving and interpreting the data from the automated slipstream analyzer and directing the refined petroleum product into a gasoline pipeline, a diesel pipeline and an intermix pipeline and wherein each of the gasoline pipeline, the diesel pipeline and the intermix pipeline has a valve.

* * * * *